United States Patent [19]
Skulic

[11] Patent Number: 5,707,006
[45] Date of Patent: Jan. 13, 1998

[54] INFANT INCUBATOR HEATER ASSEMBLY

[76] Inventor: Vedran Skulic, 7056 N. Monon Ave., Chicago, Ill. 60646

[21] Appl. No.: 703,795

[22] Filed: Aug. 27, 1996

[51] Int. Cl.⁶ .................................................. A01K 31/20
[52] U.S. Cl. ........................... 237/3; 600/22; 219/543; 392/439
[58] Field of Search ........................ 237/3, 14, 15; 219/400, 385, 386

[56] References Cited

U.S. PATENT DOCUMENTS

| | | |
|---|---|---|
| 2,347,376 | 4/1944 | Kirschbaum . |
| 2,457,028 | 12/1948 | Bors . |
| 2,648,327 | 8/1953 | Gibbon . |
| 3,079,673 | 3/1963 | Loehlein et al. . |
| 3,499,189 | 3/1970 | Perras . |
| 3,550,680 | 12/1970 | Shriver . |
| 3,919,999 | 11/1975 | Gluck et al. ........................ 128/1 |
| 3,927,301 | 12/1975 | Heuel et al. . |
| 3,937,923 | 2/1976 | Smith . |
| 4,131,785 | 12/1978 | Shutt . |
| 4,246,597 | 1/1981 | Cole et al. . |
| 4,369,835 | 1/1983 | Goudy, Jr. . |
| 5,162,038 | 11/1992 | Wilker ........................ 237/3 |
| 5,265,318 | 11/1993 | Shero . |
| 5,285,519 | 2/1994 | Barsky et al. ................... 237/3 |

*Primary Examiner*—Henry A. Bennett
*Assistant Examiner*—Derek S. Boles
*Attorney, Agent, or Firm*—Ratner & Prestia

[57] ABSTRACT

An infant incubator heater assembly having a heat radiator which is removably mounted, so that it can be removed for cleaning and maintenance. The heat radiator has a plurality of radially extending fins. In the removal and installation of the heat radiator, it slides along a cartridge heater with which the heat radiator is closely fitted for heat transfer. Preferably, the cartridge heater is mounted for self-alignment to accommodate the close fit between the heat radiator and the cartridge heater and prevent binding as the heat radiator is removed or installed.

4 Claims, 1 Drawing Sheet

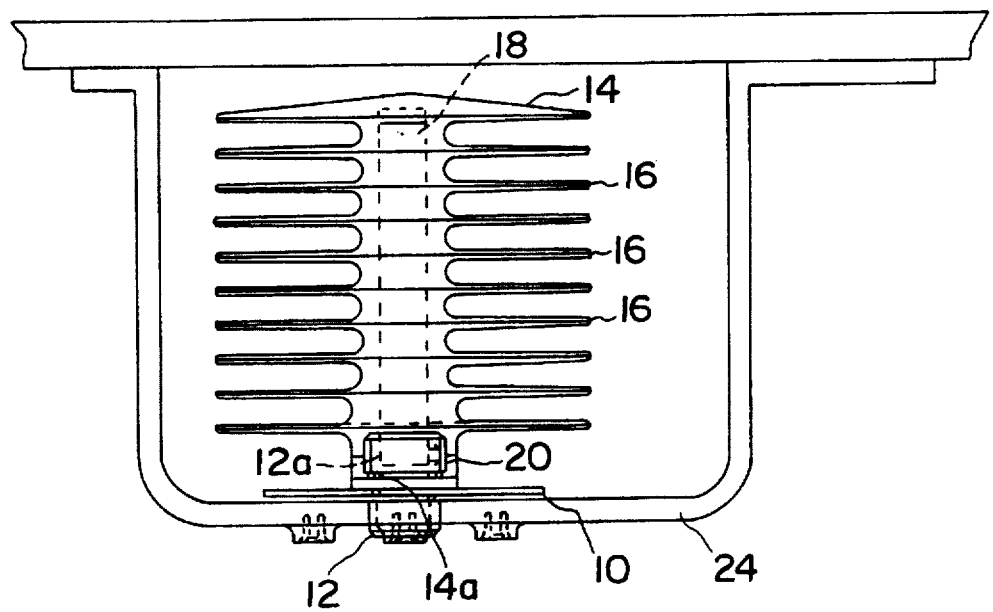
F I G. 1
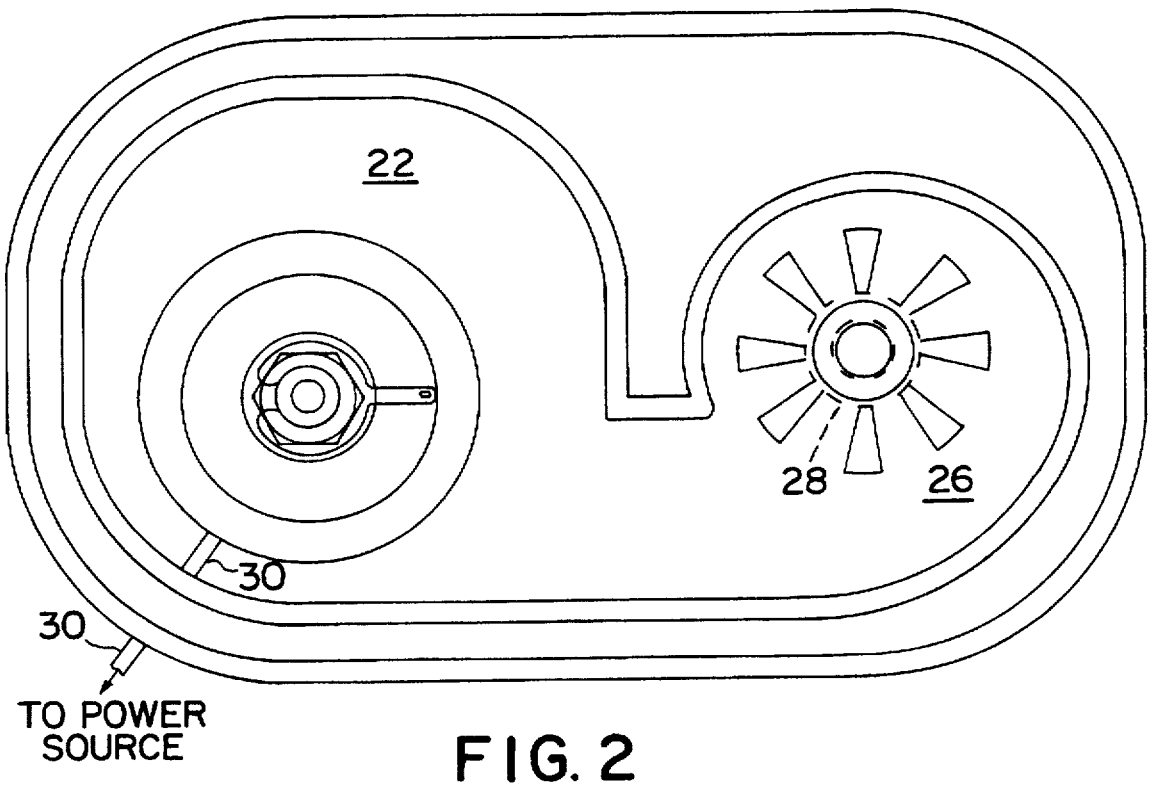
F I G. 2

INFANT INCUBATOR HEATER ASSEMBLY

TECHNICAL FIELD

The present invention relates, in general, to equipment for treating infants and, in particular, to a heater assembly for an infant incubator.

BACKGROUND OF THE INVENTION

In an infant incubator, the air delivered to the hood within which an infant is positioned should be free of contaminants. Consequently, the units which condition this air to have the desired temperature and humidity should be easily accessible for cleaning and maintenance.

SUMMARY OF THE INVENTION

An infant incubator heater assembly, constructed in accordance with the present invention, includes a mounting plate adapted for attachment to a base of an incubator and a mounting bushing mounted to the mounting plate. This infant incubator heater assembly also includes a heat radiator removably attached to the mounting bushing and having a plurality of radially extending fins and a cartridge heater extending through the heat radiator in heat transfer relationship with the heat radiator and mounted to the mounting bushing.

BRIEF DESCRIPTION OF THE DRAWINGS

FIG. 1 is a vertical side view of an infant incubator heater assembly constructed in accordance with the present invention.

FIG. 2 is a top view an infant incubator heater assembly constructed in accordance with the present invention positioned within a compartment in the base of an infant incubator.

DETAILED DESCRIPTION OF THE INVENTION

Referring to FIGS. 1 and 2, an infant incubator heater assembly, constructed in accordance with the present invention, includes a mounting plate 10 adapted for attachment to a base of an incubator and a mounting bushing 12 attached to the mounting plate. A heat radiator 14 is removably attached to mounting bushing 12 and has a plurality of radially extending fins 16.

Mounting bushing 12 has an external thread 12a and heat radiator 14 has an extension with an internal thread 14a which engages the external thread of the mounting bushing for removable attachment of the heat radiator to the mounting bushing.

A cartridge heater 18 extends through heat radiator 16 in heat transfer relationship with the heat radiator and is mounted to mounting bushing 12. Preferably, cartridge heater 18 is mounted to mounting bushing by a movable bushing 20 captive within mounting bushing 12 for floating movement and to which the cartridge heater is attached. Movable bushing 20 permits self-alignment of cartridge heater 18 and facilitates sliding of heat radiator 14 along cartridge heater 18 to prevent binding in the close fitting, required for heat transfer, between heat radiator 14 and cartridge heater 18 as the heat radiator is installed or removed.

As shown in FIG. 2, the heater assembly just described is positioned in a compartment 22 having a wall 24 (shown in FIG. 1) which is part of an incubator base and to which mounting plate 10 is attached. Positioned in an adjacent compartment 26 is a fan 28 for forcing air into compartment 22 for passage of the air past fins 16 of heat radiator 14. Power is supplied to cartridge heater 18 from a power source by means of a cable 30.

In the cleaning and maintenance of an infant incubator heater assembly, constructed in accordance with the present invention, heat radiator 14 is grasped and turned to detach the heat radiator from the mounting bushing 12. Heat radiator 14 then is moved axially of cartridge heater 18 and removed from the incubator base for cleaning or maintenance. Heat radiator 14 is installed by a reverse procedure.

While there have been described preferred embodiments of the present invention, it should be obvious to those skilled in the art that various modifications and changes can be made without departing from the true spirit and scope of the invention.

What is claimed:

1. An infant incubator heater assembly comprising:

a mounting plate adapted for attachment to a base of an incubator;

a mounting bushing mounted to said mounting plate;

a heat radiator removably attached to said mounting bushing and having a plurality of radially extending fins; and a cartridge heater extending through said heat radiator in heat transfer relationship with said heat radiator and mounted to said mounting bushing.

2. An incubator heater assembly according to claim 1 wherein:

(a) said mounting bushing has an external thread, and (b) said heat radiator has an extension with an internal thread which engages said external thread of said mounting bushing for removable attachment of said heat radiator to said mounting bushing.

3. An incubator heater assembly comprising:

a compartment;

a heater assembly positioned in said compartment and having:

(a) a mounting plate adapted for attachment to a wall of said compartment, (b) a mounting bushing mounted to said mounting plate, (c) a heat radiator removably attached to said mounting bushing and having a plurality of radially extending fins, and (d) a cartridge heater extending through said heat radiator in heat transfer relationship with said heat radiator and mounted to said mounting bushing;

a fan for forcing air into said compartment for passage of said air past said fins of said heat radiator; and means for supplying power to said cartridge heater.

4. An incubator heater assembly according to claim 3 wherein:

(a) said mounting bushing has an external thread, and (b) said heat radiator has an extension with an internal thread which engages said external thread of said mounting bushing for removable attachment of said heat radiator to said mounting bushing.

* * * * *

UNITED STATES PATENT AND TRADE MARK OFFICE
CERTIFICATE OF CORRECTION

PATENT NO.   :   5,707,006
DATED        :   January 13, 1998
INVENTOR(S)  :   Vedran Skulic It is certified that error appears in the above-identified patent and that said Letters Patent is hereby corrected as shown below:

item [56] References Cited, please delete:

"2,347,376     4/1944     Kirschbaum"

and substitute therefor:

--2,347,326     4/1944     Kirschbaum--

Signed and Sealed this

Ninth Day of June, 1998

Attest:

BRUCE LEHMAN

Attesting Officer

Commissioner of Patents and Trademarks